United States Patent
Christensen

(10) Patent No.: US 8,034,121 B2
(45) Date of Patent: Oct. 11, 2011

(54) PROSTHETIC FOOT WITH TWO LEAF-SPRINGS JOINED AT HEEL AND TOE

(75) Inventor: Roland J. Christensen, Fayette, UT (US)

(73) Assignee: Freedom Innovations, LLC, Irvine, CA (US)

( * ) Notice: Subject to any disclaimer, the term of this patent is extended or adjusted under 35 U.S.C. 154(b) by 16 days.

(21) Appl. No.: 12/425,876

(22) Filed: Apr. 17, 2009

(65) Prior Publication Data

US 2009/0265019 A1    Oct. 22, 2009

Related U.S. Application Data

(60) Provisional application No. 61/124,687, filed on Apr. 18, 2008.

(51) Int. Cl.
*A61F 2/66* (2006.01)

(52) U.S. Cl. ............................................ 623/55; 623/53

(58) Field of Classification Search .................... 623/55; 482/76–80
See application file for complete search history.

(56) References Cited

U.S. PATENT DOCUMENTS

| | | | |
|---|---|---|---|
| 42,799 A | 5/1864 | Shepard | |
| 92,031 A | 6/1869 | Foster | |
| 292,800 A | 2/1884 | Furrer | |
| 497,026 A | 5/1893 | Judson | |
| 1,001,641 A | 8/1911 | Harrison | |
| 1,191,633 A | 7/1916 | White | |
| 1,289,580 A | 12/1918 | Vincenti | |
| 1,354,427 A | 9/1920 | Welter | |
| 1,779,765 A | 10/1930 | Eichhorn | |
| 1,996,874 A | 4/1935 | Mascau | |
| 2,036,830 A | 4/1936 | Rowley | |
| 2,050,973 A * | 8/1936 | Andrew Kurtz | 36/156 |
| 2,101,265 A | 12/1937 | Mercier | |
| 2,379,538 A | 7/1945 | Meierhofer | |
| 2,443,356 A | 6/1948 | Mathis | |
| 2,453,969 A | 11/1948 | Carter | |
| 2,470,480 A | 5/1949 | Fogg | |
| 2,570,735 A | 10/1951 | Weise | |
| 2,617,115 A | 11/1952 | Ellery | |

(Continued)

FOREIGN PATENT DOCUMENTS

BR    9304225 A    7/1995

(Continued)

OTHER PUBLICATIONS

Christensen, U.S. Appl. No. 11/270,212, filed Nov. 8, 2005.

(Continued)

*Primary Examiner* — Thomas J Sweet
*Assistant Examiner* — Jacqueline Woznicki
(74) *Attorney, Agent, or Firm* — Thorpe North & Western LLP

(57) ABSTRACT

A prosthetic foot includes a pair of elongated forefoot leaf springs with proximal ends coupled to an attachment member and extending in an arc to distal ends with the forefoot leaf springs being oriented with one over another. The pair of forefoot leaf springs has different lengths and is coupled to one another at the proximal and distal ends defining an open, uninterrupted gap between the forefoot leaf springs. A pair of hinge connections can be disposed each at a different one of the proximal and distal ends of the pair of elongated forefoot leaf springs. The pair of forefoot leaf springs together has a non-linear force deflection under loading during gait.

9 Claims, 4 Drawing Sheets

Fig. 6

U.S. PATENT DOCUMENTS

| | | | |
|---|---|---|---|
| 2,640,200 A | 6/1953 | Wisbrun | |
| 2,843,853 A | 6/1958 | Mauch | |
| 2,973,969 A | 3/1961 | Thall | |
| 3,206,235 A | 9/1965 | Albinson et al. | |
| 3,379,430 A | 4/1968 | Ransom | |
| 3,548,420 A | 12/1970 | Spence | |
| 3,551,914 A | 1/1971 | Woodall | |
| 3,754,286 A | 8/1973 | Ryan | |
| 3,858,379 A | 1/1975 | Graves et al. | |
| 3,871,032 A | 3/1975 | Karas | |
| 3,874,004 A | 4/1975 | May | |
| 3,906,552 A | 9/1975 | Weber | |
| 3,920,610 A | 11/1975 | Wagner | |
| 3,956,775 A | 5/1976 | Moore | |
| 3,982,280 A | 9/1976 | Asbelle et al. | |
| 4,089,072 A | 5/1978 | Glabiszewski | |
| 4,328,594 A | 5/1982 | Campbell et al. | |
| 4,341,222 A | 7/1982 | Gardineer et al. | |
| 4,442,554 A | 4/1984 | Copes | |
| 4,499,613 A | 2/1985 | Yarrow | |
| 4,506,395 A | 3/1985 | Haupt | |
| 4,517,968 A | 5/1985 | Greene et al. | |
| 4,547,913 A | 10/1985 | Phillips | |
| 4,606,332 A | 8/1986 | Gibson | |
| 4,636,220 A | 1/1987 | Ziegelmeyer | |
| 4,645,509 A | 2/1987 | Poggi et al. | |
| 4,676,800 A | 6/1987 | Chen | |
| 4,676,801 A | 6/1987 | Lundeen | |
| 4,688,559 A | 8/1987 | Vito et al. | |
| 4,721,510 A | 1/1988 | Cooper et al. | |
| 4,764,172 A | 8/1988 | McCoy | |
| 4,793,450 A | 12/1988 | Saveniji | |
| 4,822,363 A | 4/1989 | Phillips | |
| 4,852,863 A | 8/1989 | Breitenbacher et al. | |
| 4,865,611 A | 9/1989 | Al-Turaiki | |
| 4,865,612 A | 9/1989 | Arbogast et al. | |
| 4,869,476 A | 9/1989 | Shtarkman | |
| 4,892,553 A | 1/1990 | Prahl | |
| 4,938,775 A | 7/1990 | Morgan | |
| 4,938,777 A | 7/1990 | Mason et al. | |
| 4,959,073 A | 9/1990 | Merlette | |
| 4,986,393 A | 1/1991 | Preukschate et al. | |
| 5,007,938 A | 4/1991 | Prahl | |
| 5,019,109 A | 5/1991 | Voisin | |
| 5,030,239 A | 7/1991 | Copes | |
| 5,037,444 A | 8/1991 | Phillips | |
| 5,062,859 A | 11/1991 | Naeder | |
| 5,088,479 A | 2/1992 | DeToro | |
| 5,112,356 A | 5/1992 | Harris et al. | |
| 5,116,383 A | 5/1992 | Shorter et al. | |
| 5,116,384 A | 5/1992 | Wilson et al. | |
| 5,156,632 A | 10/1992 | Wellershaus | |
| 5,181,932 A | 1/1993 | Phillips | |
| 5,181,933 A | 1/1993 | Phillips | |
| 5,217,500 A | 6/1993 | Phillips | |
| 5,219,324 A | 6/1993 | Hall | |
| 5,219,365 A | 6/1993 | Sabolich | |
| 5,226,875 A | 7/1993 | Johnson | |
| 5,258,039 A | 11/1993 | Goh et al. | |
| 5,267,633 A | 12/1993 | Endo et al. | |
| 5,290,319 A | 3/1994 | Phillips | |
| 5,314,499 A | 5/1994 | Collier, Jr. | |
| 5,376,133 A | 12/1994 | Gramnas | |
| 5,376,139 A | 12/1994 | Pitkin | |
| 5,376,141 A | 12/1994 | Phillips | |
| 5,387,246 A | 2/1995 | Phillips | |
| 5,405,408 A | 4/1995 | Pitkin | |
| 5,405,411 A | 4/1995 | McCoy | |
| 5,425,781 A | 6/1995 | Allard et al. | |
| 5,425,782 A | 6/1995 | Phillips | |
| 5,429,588 A | 7/1995 | Young et al. | |
| 5,443,528 A | 8/1995 | Allen | |
| 5,443,529 A | 8/1995 | Phillips | |
| 5,449,150 A | 9/1995 | Watanabe et al. | |
| 5,458,656 A | 10/1995 | Phillips | |
| 5,464,441 A | 11/1995 | Phillips | |
| 5,482,513 A | 1/1996 | Wilson | |
| 5,486,157 A | 1/1996 | DiBenedetto | |
| 5,486,209 A | 1/1996 | Phillips | |
| 5,507,838 A | 4/1996 | Chen | |
| 5,509,936 A | 4/1996 | Rappoport et al. | |
| 5,509,937 A | 4/1996 | Allard et al. | |
| 5,509,938 A | 4/1996 | Phillips | |
| 5,514,185 A | 5/1996 | Phillips | |
| 5,514,186 A | 5/1996 | Phillips | |
| 5,545,127 A | 8/1996 | DeToro | |
| 5,549,714 A | 8/1996 | Phillips | |
| 5,571,210 A | 11/1996 | Lindh | |
| 5,571,213 A | 11/1996 | Allen | |
| 5,593,455 A | 1/1997 | Phillips | |
| 5,593,456 A | 1/1997 | Merlette | |
| 5,593,457 A | 1/1997 | Phillips | |
| 5,609,568 A | 3/1997 | Andrews | |
| 5,645,138 A | 7/1997 | Tajima et al. | |
| 5,653,767 A | 8/1997 | Allen et al. | |
| 5,653,768 A | 8/1997 | Kania | |
| 5,695,526 A | 12/1997 | Wilson | |
| 5,701,686 A * | 12/1997 | Herr et al. | 36/27 |
| 5,725,598 A | 3/1998 | Phillips | |
| 5,728,175 A | 3/1998 | Rincoe | |
| 5,728,176 A | 3/1998 | Phillips | |
| 5,728,177 A | 3/1998 | Phillips | |
| 5,746,774 A | 5/1998 | Kramer et al. | |
| 5,766,265 A | 6/1998 | Phillips | |
| 5,766,704 A | 6/1998 | Allen et al. | |
| 5,769,896 A | 6/1998 | Rosendahl et al. | |
| 5,776,205 A | 7/1998 | Phillips | |
| 5,779,735 A | 7/1998 | Molino | |
| 5,800,564 A | 9/1998 | Gelineau | |
| 5,800,565 A | 9/1998 | Biedermann | |
| 5,800,569 A | 9/1998 | Phillips | |
| 5,824,112 A | 10/1998 | Phillips | |
| 5,888,238 A | 3/1999 | Phillips et al. | |
| 5,893,891 A | 4/1999 | Zahedi | |
| 5,897,515 A | 4/1999 | Willner et al. | |
| 5,899,944 A | 5/1999 | Phillips | |
| 5,913,902 A | 6/1999 | Geible | |
| 5,944,679 A | 8/1999 | DeToro | |
| 5,944,760 A * | 8/1999 | Christensen | 623/55 |
| 5,957,981 A | 9/1999 | Gramnas | |
| 5,976,191 A | 11/1999 | Phillips | |
| 5,993,488 A | 11/1999 | Phillips | |
| 6,007,582 A | 12/1999 | May | |
| 6,019,741 A | 2/2000 | Prieskorn | |
| 6,019,795 A | 2/2000 | Phillips | |
| 6,071,313 A | 6/2000 | Phillips | |
| 6,077,301 A | 6/2000 | Pusch | |
| 6,083,184 A | 7/2000 | Kenosh | |
| 6,099,572 A * | 8/2000 | Mosler et al. | 623/53 |
| 6,120,547 A | 9/2000 | Christensen | |
| 6,146,344 A | 11/2000 | Bader | |
| 6,165,227 A | 12/2000 | Phillips | |
| 6,187,052 B1 | 2/2001 | Molino et al. | |
| 6,197,068 B1 | 3/2001 | Christensen | |
| 6,206,934 B1 | 3/2001 | Phillips | |
| 6,228,124 B1 | 5/2001 | Slemker et al. | |
| 6,241,776 B1 * | 6/2001 | Christensen | 623/52 |
| 6,245,035 B1 | 6/2001 | Schrijver | |
| 6,254,643 B1 | 7/2001 | Phillips | |
| 6,261,324 B1 | 7/2001 | Merlette | |
| 6,267,742 B1 | 7/2001 | Krivosha et al. | |
| 6,280,479 B1 | 8/2001 | Phillips | |
| 6,290,730 B1 | 9/2001 | Pitkin et al. | |
| 6,302,858 B1 | 10/2001 | DeToro et al. | |
| 6,306,178 B1 | 10/2001 | Kania et al. | |
| D457,639 S | 5/2002 | McCoy | |
| 6,402,790 B1 | 6/2002 | Celebi | |
| 6,406,500 B1 | 6/2002 | Phillips | |
| 6,443,993 B1 | 9/2002 | Koniuk | |
| 6,443,995 B1 | 9/2002 | Townsend et al. | |
| 6,514,293 B1 | 2/2003 | Jang et al. | |
| 6,562,075 B2 | 5/2003 | Townsend et al. | |
| 6,596,029 B1 | 7/2003 | Gramnas | |
| 6,602,295 B1 * | 8/2003 | Doddroe et al. | 623/55 |
| 6,663,673 B2 | 12/2003 | Christensen | |
| 6,669,737 B2 | 12/2003 | Mosler et al. | |
| 6,676,618 B2 | 1/2004 | Andersen | |

| | | |
|---|---|---|
| 6,676,708 B1 | 1/2004 | Laghi |
| 6,702,858 B2 | 3/2004 | Christensen |
| 6,740,125 B2 | 5/2004 | Mosler |
| 6,767,370 B1 | 7/2004 | Mosler et al. |
| 6,793,683 B1 | 9/2004 | Laghi |
| 6,805,717 B2 | 10/2004 | Christensen |
| 6,811,571 B1 | 11/2004 | Phillips |
| 6,869,451 B1 | 3/2005 | Laghi |
| 6,875,241 B2 | 4/2005 | Christesen |
| 6,875,242 B2 | 4/2005 | Christensen |
| 6,887,213 B2 | 5/2005 | Smits |
| 6,887,279 B2 | 5/2005 | Phillips et al. |
| 6,899,737 B1 | 5/2005 | Phillips et al. |
| 6,911,051 B2 | 6/2005 | Cheng |
| 6,911,052 B2 | 6/2005 | Christensen |
| 6,929,665 B2 | 8/2005 | Christensen |
| 6,942,702 B2 | 9/2005 | Mitsugi et al. |
| 6,942,704 B2 | 9/2005 | Sulprizio |
| 6,945,947 B2 | 9/2005 | Ingimundarson et al. |
| 6,964,119 B2 * | 11/2005 | Weaver, III .................. 36/27 |
| 6,966,933 B2 | 11/2005 | Christensen |
| 6,972,043 B1 * | 12/2005 | Biedermann et al. .......... 623/55 |
| 7,077,818 B2 | 7/2006 | Ingimundarson et al. |
| 7,172,630 B2 | 2/2007 | Christensen |
| 7,266,910 B2 | 9/2007 | Ingimundarson |
| 7,341,603 B2 | 3/2008 | Christensen |
| 7,347,877 B2 | 3/2008 | Clausen et al. |
| 7,354,456 B2 | 4/2008 | Phillips |
| 7,279,011 B2 | 5/2008 | Ham et al. |
| 7,410,503 B2 * | 8/2008 | Townsend et al. ............. 623/53 |
| 7,419,509 B2 | 9/2008 | Christensen |
| 7,462,201 B2 | 12/2008 | Christensen |
| 7,507,259 B2 * | 3/2009 | Townsend et al. ............. 623/52 |
| 7,520,904 B2 | 4/2009 | Christensen |
| 7,572,299 B2 | 8/2009 | Christensen |
| 7,618,464 B2 | 11/2009 | Christensen |
| 7,686,848 B2 | 3/2010 | Christensen |
| 7,727,285 B2 | 6/2010 | Christensen |
| 7,740,602 B2 | 6/2010 | Christensen |
| 7,794,506 B2 | 9/2010 | Christensen |
| 7,824,446 B2 | 11/2010 | Christensen |
| 2002/0077706 A1 | 6/2002 | Phillips |
| 2002/0133237 A1 | 9/2002 | Christensen |
| 2003/0045944 A1 | 3/2003 | Mosler et al. |
| 2003/0120353 A1 | 6/2003 | Christensen |
| 2003/0120354 A1 * | 6/2003 | Doddroe et al. .............. 623/55 |
| 2003/0191540 A1 | 10/2003 | Townsend et al. |
| 2004/0064046 A1 | 4/2004 | Shehada |
| 2004/0068326 A1 | 4/2004 | Christensen |
| 2004/0102727 A1 | 5/2004 | Smits |
| 2004/0134500 A1 | 7/2004 | Ingimundarson et al. |
| 2004/0162623 A1 | 8/2004 | Phillips |
| 2004/0243253 A1 * | 12/2004 | Cool et al. .................. 623/52 |
| 2005/0049721 A1 * | 3/2005 | Sulprizio .................... 623/52 |
| 2005/0171618 A1 | 8/2005 | Christensen |
| 2005/0197717 A1 | 9/2005 | Ragnarsdottir et al. |
| 2005/0203640 A1 | 9/2005 | Christensen |
| 2005/0216098 A1 | 9/2005 | Christensen |
| 2005/0234378 A1 | 10/2005 | Ingimundarson et al. |
| 2005/0261783 A1 | 11/2005 | Geilman et al. |
| 2006/0030950 A1 | 2/2006 | Townsend |
| 2006/0241783 A1 | 10/2006 | Christensen |
| 2008/0167730 A1 * | 7/2008 | Pusch .......................... 623/53 |
| 2009/0281638 A1 * | 11/2009 | Tourneux ..................... 623/55 |
| 2010/0023135 A1 * | 1/2010 | Rubie et al. .................. 623/55 |
| 2011/0009982 A1 * | 1/2011 | King et al. ................... 623/53 |

FOREIGN PATENT DOCUMENTS

| | | |
|---|---|---|
| BR | 9304552-2 | 11/1995 |
| CA | 2 266 113 | 10/1999 |
| DE | 295807 | 12/1916 |
| EP | 1 149 568 | 10/2001 |
| EP | 1340478 | 9/2003 |
| GB | 1191633 | 5/1970 |
| GB | 1550-658 | 8/1979 |
| GB | 2244006 | 11/1991 |
| IT | 556381 | 11/1958 |
| JP | 55112440 | 8/1980 |
| JP | 57040138 | 3/1982 |
| JP | 63231031 | 9/1988 |
| RU | 2033772 | 4/1995 |
| SU | 560606 | 7/1977 |
| WO | WO 94/10942 | 5/1994 |
| WO | WO 02/30340 | 4/2002 |
| WO | WO 03/003953 | 1/2003 |

OTHER PUBLICATIONS

Christensen, U.S. Appl. No. 12/211,600, filed Sep. 16, 2008.
Christensen, U.S. Appl. No. 11/109,320, filed Apr. 18, 2005.
Christensen, U.S. Appl. No. 12/011,026, filed Jan. 22, 2008.
Christensen, U.S. Appl. No. 12/006,801, filed Jan. 4, 2008.
Christensen, U.S. Appl. No. 11/499,863, filed Aug. 3, 2006.
Christensen, U.S. Appl. No. 11/999,734, filed Dec. 5, 2007.
www.oandp.org/jpo/library/2000_01_009.asp, "Comparison of the Seattle Lite Foot and Genesis II Prosthetic Foot during walking and running." American Academy of Orthotists and Prosthetists, 2000, pp. 9-14, vol. 12, No. 1.
www.micacorp.com/products/genesis2/, MICA Manufacturing Corporation, Genesis II Prosthetic Foot, Nov. 24, 2004, 1 page.
U.S. Appl. No. 12/826,174, filed Jun. 29, 2010; Roland J. Christensen.
U.S. Appl. No. 09/607,494, filed Jun. 30, 2000; Roland J. Christensen.

* cited by examiner

PROSTHETIC FOOT WITH TWO LEAF-SPRINGS JOINED AT HEEL AND TOE

PRIORITY CLAIM

Priority is claimed to copending U.S. Provisional Patent Application Ser. No. 61/124,687, filed Apr. 18, 2008, which is hereby incorporated herein by reference in its entirety.

BACKGROUND

1. Field of the Invention

The present invention relates to a resilient prosthetic foot that has a reinforcement member to provide reinforcement. More particularly, the present invention relates to a prosthetic foot having at least a resilient forefoot member, and at least one resilient reinforcement member.

2. Related Art

Many individuals have lost a limb for various reasons including war, accident, or disease. In most instances these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. For example, see U.S. Pat. No. 4,547,913 or 5,593,456. As the user steps onto the foot, the user's weight compresses the spring. As the user moves forward, the user's weight comes off the foot and the energy stored in the spring is used to propel the user forward.

The stiffness of prosthetic feet typically varies according to the intended use. Feet intended for everyday use typically require a soft feel, and thus incorporate a loose spring. Feet intended for athletic use typically require strength, and thus incorporate a stiff spring. Although different prosthetic feet may be changed to suit the particular activity, such switching is inconvenient and at times it is impossible, such as a sudden need to run to catch, or avoid being hit by a bus. Feet designed for particular purposes are typically unsuited for other purposes. Stiff, athletic feet are too hard for everyday use, and loose, everyday feet are too fragile for athletic use. Multiple-use feet have been designed which are capable of many different uses, but without being particularly well suited for any use.

In addition, the performance of these energy storing feet has been altered in various ways to provide a more universal foot which is capable of many different uses ranging from athletic use to more normal walking. For example, some feet use multiple springs, bladders or resilient materials disposed between various elements, and/or multiple springs that deflect at different intervals of foot deflection in order to increase resistance as the force applied to the foot by the user increases. In this way, a prosthetic foot can provide a stiff or highly resilient response when a high load is applied, such as when the user runs, or a looser less resilient response when a lower load is applied, such as when the user walks. For example, see U.S. Pat. No. 6,241,776 or 6,099,572, both of which propose multiple members; one of which disposes an adjustable pressure buffer between members; the other of which places a secondary member in the extreme range of motion of a primary member.

While many prosthetic feet have been designed to accommodate variation in terrain and use, there is still a need to increase the amount of energy a prosthetic foot can store during use which can be returned to the user to help propel the user forward.

SUMMARY OF THE INVENTION

It has been recognized that it would be advantageous to develop a prosthetic foot with a non-linear force deflection under loading during gait.

The invention provides a prosthetic foot including an attachment member configured to be attached to a stump of an amputee at or above an ankle location of a natural foot. A pair of elongated forefoot leaf springs has a proximal end coupled to the attachment member, and extends in an arc to a distal end at a toe location of a natural foot. The forefoot leaf springs are oriented with one over another. Each of the pair of forefoot leaf springs has a different length and is coupled to one another at the proximal and distal ends defining an open, uninterrupted gap between the forefoot leaf springs. The pair of forefoot leaf springs together has a non-linear force deflection under loading during gait.

In accordance with a more detailed aspect of the present invention, the proximal and distal ends of the pair of forefoot leaf springs can be coupled together by a pair of hinge connections.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The embodiments of the present invention generally described herein provide for a prosthetic foot device having a primary lower elongated foot leaf spring and a secondary upper elongated forefoot leaf spring disposed above the lower forefoot leaf spring. The lower forefoot leaf spring can extend from an ankle section positioned at the ankle location of a natural foot downwardly and forwardly to a toe section positioned at the toe location of a natural foot. The lower forefoot leaf spring can be smoothly curved and can form an arc between the ankle section and the toe section. The upper forefoot leaf spring can be coupled to the lower forefoot leaf spring at the ankle section and at the toe location. The leaf springs can be coupled at their proximal and distal ends by hinge connections. The upper forefoot leaf spring can extend in a smooth curve downwardly and forwardly from the ankle location to the toe location and can form an arc between the ankle section and the toe section. The arc of the upper forefoot leaf spring can have a shorter arc length and/or radius of curvature than the arc of the lower forefoot leaf spring and an open, uninterrupted gap between the forefoot leaf springs can be formed between the lower and upper forefoot leaf springs. The lower and upper forefoot leaf springs can be flexible to store energy and resilient to return energy, and the open, uninterrupted gap between the forefoot leaf springs allows the intermediate portion of the forefoot leaf springs to move freely with respect to one another during deflection so that the pair of forefoot leaf springs together having a non-linear force deflection under loading during gait.

In use, when a user steps down on the prosthetic foot of the present invention, the toe section of the lower forefoot leaf spring can be deflected upward which in turn deflects the toe section of the upper forefoot leaf spring. The lower forefoot leaf spring can store energy during the deflection and the upper forefoot leaf spring can store additional energy during deflection. The energy stored by the forefoot leaf springs can be returned to the user when the user lifts the prosthetic foot. In this way, the prosthetic foot of the present invention can propel the user's step.

Figure 1:
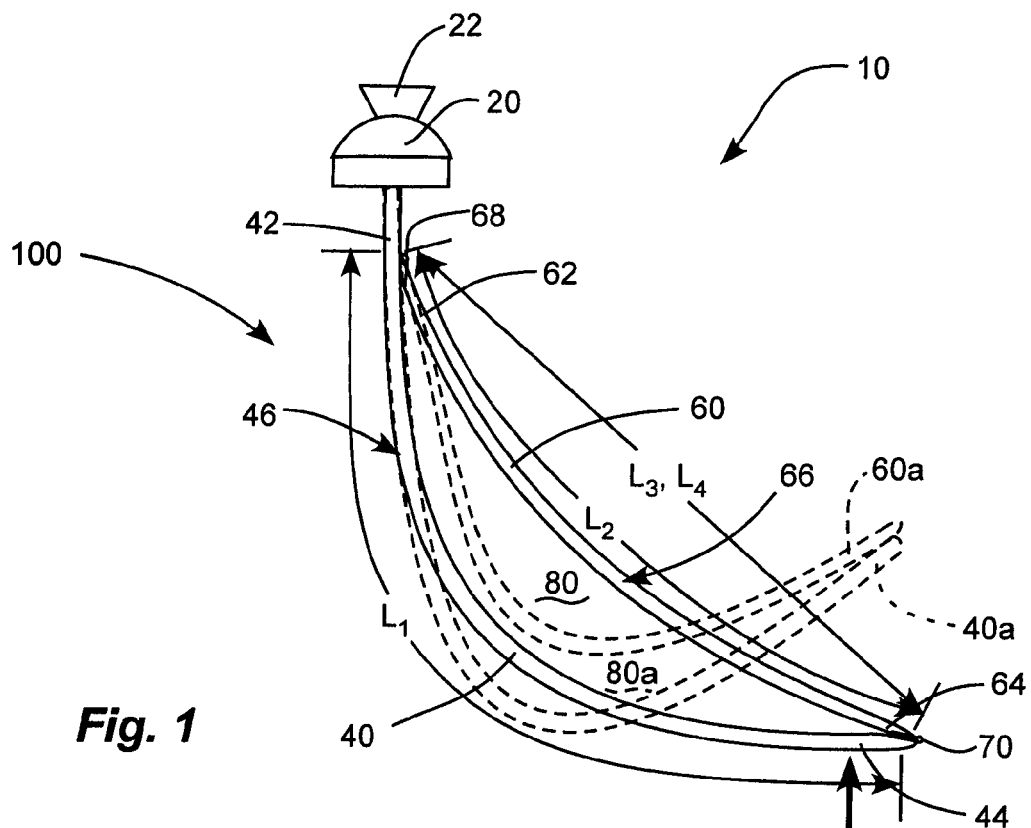
FIG. 1 is a side view of a prosthetic foot device in accordance with an embodiment of the present invention.
Figure 2:
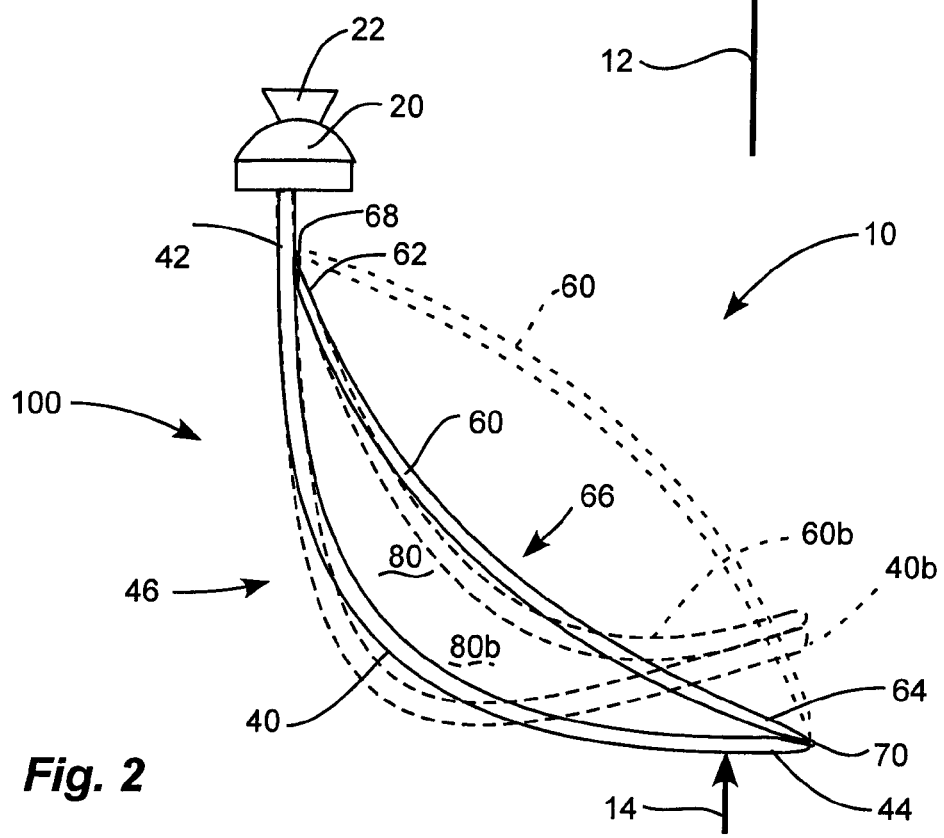
FIG. 2 is a side view of the prosthetic foot device of FIG. 1.

As illustrated in FIGS. 1-2, a prosthetic foot device, indicated generally at 10, is shown in accordance with an embodiment of the present invention for use by an amputee. The prosthetic foot device 10 can have a proximal end or an attachment section, indicated generally at 20, an elongated primary lower forefoot leaf spring 40, and an elongated secondary upper forefoot leaf spring 60.

The attachment section 20 can include an attachment member 22, such as a connector or coupler, configured to attach to the stump of an amputee, or a socket to receive the stump. The attachment member can have a frustroconical connector, pyramidal connector, or the like. The attachment member can be located at or above an ankle location of a natural foot.

The lower forefoot leaf spring 40 can extend from the attachment member to a toe location of a natural foot. The lower forefoot leaf spring 40 can have a proximal end or an ankle section 42 positioned at the ankle location and a distal end or a toe section 44 positioned at the toe location. The lower forefoot leaf spring 40 can form a smooth and curving arc, indicated generally at 46, sloping downwardly and forwardly from the ankle section 42 to the toe section 44.

The upper forefoot leaf spring 60 can also extend approximately between the ankle location and the toe location of a natural foot. The upper forefoot leaf spring can be coupled to the lower forefoot leaf spring between the toe section and the ankle section of the lower forefoot leaf spring. The upper forefoot leaf spring 60 can have a proximal end or an ankle section 62 positioned near the ankle location and or a distal end a toe section 64 positioned near the toe location. In one aspect, the ankle section 62 of the upper forefoot leaf spring 60 can be coupled to the lower forefoot leaf spring at or near the ankle section 42 of the lower forefoot leaf spring 40.

Similarly, the toe section 64 of the upper forefoot leaf spring 60 can be coupled to the lower forefoot leaf spring 40 at or near the toe section 44 of the lower forefoot leaf spring. The upper forefoot leaf spring 60 can form a smooth and curving arc, indicated generally at 66, that slopes downwardly and forwardly from the ankle section 62 to the toe section 64. The secondary foot member 60 can be arcuate and bend towards the lower forefoot leaf spring in a concave configuration (as shown in solid lines); or can be arcuate and bend away from the primary foot member in a convex configuration (as shown in dashed lines in FIG. 2).

Additionally, the forefoot leaf springs 40 and 60 can include a composite material with fiber in a resin matrix. For example, the forefoot leaf springs can be formed of carbon fibers, fiberglass, and the like, with a resin such as epoxy. The composite material can be shaped to form the arc 46 and 66 of the forefoot leaf springs and can form a curvilinear spring member that is flexible to store energy and resilient to return energy.

The attachment of the lower and/or upper forefoot leaf springs to the attachment member can be essentially vertical, as shown in FIGS. 1 and 2. At least one of the forefoot leaf spring, such as the lower forefoot leaf spring, can have an essentially vertical attachment.

The proximal and distal ends of the forefoot leaf springs are coupled together in that the ends of each move together. In addition, the ends can be directly coupled to one another without any spacers. In addition, the proximal and distal ends can be coupled together with hinged connections 68 and 70 or movable or pivotal joint, such as a piano type hinge with a pivot, a living hinge with a flexible web, or the like. The hinged connections maintain the coupled or fixed relationship between the proximal and distal ends of the forefoot leaf springs so that they move together, but allowing the ends to pivot with respect to one another. The hinged connections between the proximal and distal ends can be in the area of the proximal and distal ends in the area of the attachment area and toe location, not necessarily at the extreme proximal and distal ends.

The arc 66 formed by the upper forefoot leaf spring 60 can have a shorter arc length, $L_2$, than the arc length, $L_1$, of the arc 46 formed by the lower forefoot leaf spring 40 such that the upper forefoot leaf spring 60 is variably spaced apart from the lower forefoot leaf spring 40 between the couplings at the ankle section 62 and the toe section 64. Additionally, a chord length, $L_3$, between the ankle section 42 and toe section 44 of the lower forefoot leaf spring 40 and a chord length, $L_4$, between the ankle section 62 and the toe section 64 of the upper forefoot leaf spring 60 can be substantially equal in length. In this way, a crescent shaped space 80 can be formed between the pair of forefoot leaf springs. In addition, an open, uninterrupted gap 80 or space is defined between the forefoot leaf springs. Thus, the intermediate portions of the pair of forefoot leaf springs are free to move with respect to one another during deflection.

In use, when a user steps down on the prosthetic foot 10, the toe section 44 of the lower forefoot leaf spring 40 can be deflected upward which compresses the arc 46 or curvilinear spring of the lower forefoot leaf spring such that energy is stored in the forefoot leaf spring by the deflection. Deflection of the toe section 44 of the lower forefoot leaf spring 40 can also deflect the toe section 64 of the upper forefoot leaf spring 60 such that the arc 66 or curvilinear spring of the upper forefoot leaf spring is also compressed to store additional energy in the forefoot leaf spring. When a relatively larger load is applied to the foot during the stepping motion, as indicated by the arrow at 12 in FIG. 1, the lower forefoot leaf spring 40 and the upper forefoot leaf spring 60 can deflect a greater distance, as indicated by dashed lines 40a and 60a. Additionally, when a relatively smaller load is applied to the foot during the stepping motion, as indicated by the arrow at 14 in FIG. 2, the lower forefoot leaf spring 40 and the upper forefoot leaf spring 60 can deflect a shorter distance, as indicated by dashed lines 40b and 60b.

Figure 3:
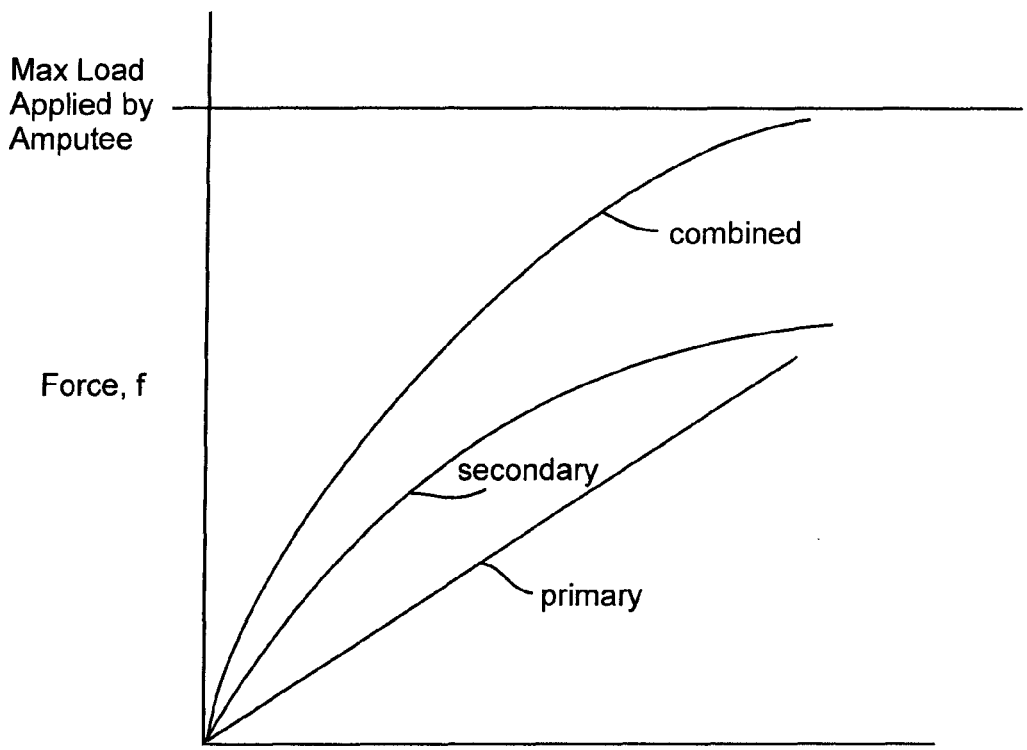
FIG. 3 is a force deflection diagram showing the total force required to achieve a given deflection for a primary lower forefoot leaf spring, a secondary upper forefoot leaf spring, and combined forefoot leaf springs for the prosthetic foot device of FIG. 1.

As shown in FIG. 3, a given force applied to the lower forefoot leaf spring 40 will result in a given deflection of the lower forefoot leaf spring. Similarly, a given force applied to the upper forefoot leaf spring 60 will result in a given deflection of the upper forefoot leaf spring. With the upper forefoot leaf spring 60 coupled to the lower forefoot leaf spring 40, a greater force can be required to achieve the same deflection of the lower forefoot leaf spring than when the lower forefoot leaf spring is deflected alone.

Figure 4:
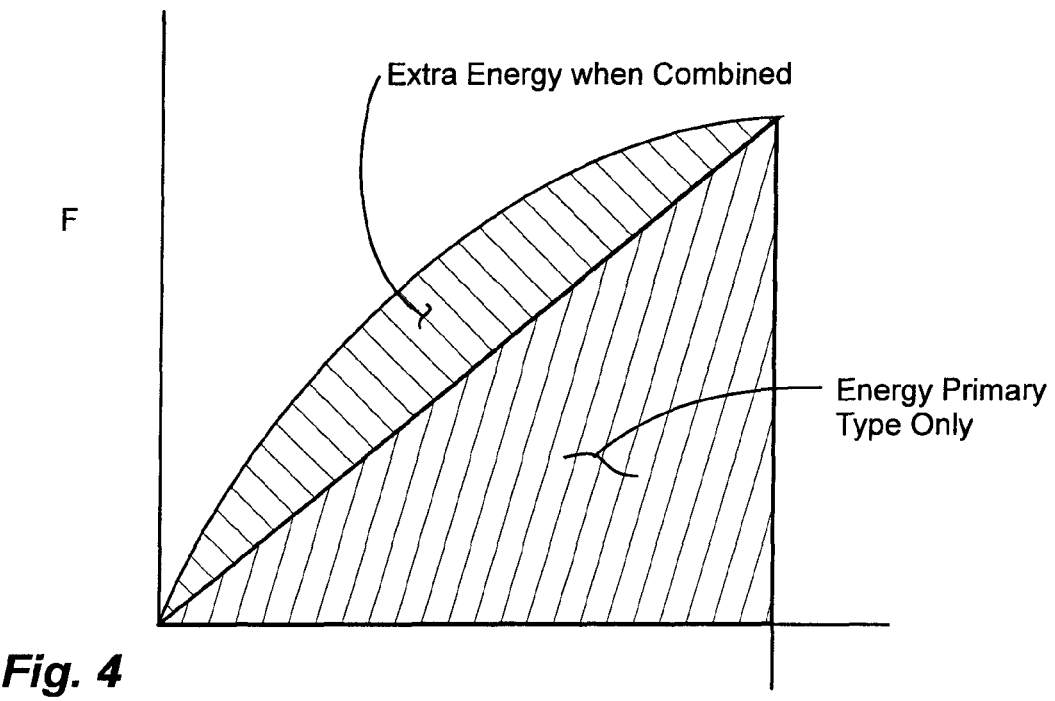
FIG. 4 is an energy plot of the force deflection diagram of FIG. 3 showing the amount of energy stored in the forefoot leaf springs of the prosthetic foot of FIG. 1 for a given deflection.

Similarly, it will be appreciated that the lower forefoot leaf spring 40 can store energy when deflected, and the upper forefoot leaf spring 60 can store additional energy during deflection. Specifically, as illustrated in FIG. 4, the lower forefoot leaf spring 40 can store the amount of energy depicted under the force deflection curve labeled for the lower forefoot leaf spring for any given force applied. Additionally, the upper forefoot leaf spring 60 can store the additional amount of energy depicted under the force deflection curve labeled for the upper forefoot leaf spring. The energy stored by the lower forefoot leaf spring can be added to the energy stored in the upper forefoot leaf spring so that the total amount of energy stored by the prosthetic foot device is the amount of energy shown under both the force deflection curves. In this way, the pair of forefoot leaf springs can increase the amount of energy available for use by the amputee as compared to a single forefoot leaf spring. The energy stored by the lower and upper forefoot leaf springs 40 and 60 can be returned to the user when the user lifts up on the prosthetic foot 10. In this way, the prosthetic foot 10 of the present invention can help to propel the user's step.

Additionally, the gap 80 or crescent shaped space between the forefoot leaf springs can change size as the forefoot leaf springs are compressed. For example, the crescent shaped space 80 can have a relatively smaller cross section 80a when the lower forefoot leaf spring 40 and the upper forefoot leaf spring 60 are deflected under a relatively greater load, indicated by the arrow at 12, as shown in FIG. 1. Similarly, the crescent shaped space 80 can have a relatively larger cross section 80b when the lower forefoot leaf spring 40 and the upper forefoot leaf spring 60 are deflected under a relatively smaller load, indicated by the arrow at 14, as shown in FIG. 2. Thus, the forefoot leaf springs can work together to form a crescent shaped spring.

It will be appreciated that each member of the crescent shaped spring can have different spring characteristics. For example, the lower forefoot leaf spring 40 can have a linear or constant force to deflection ratio such that the lower forefoot leaf spring can deflect by a constant proportional amount with respect to any given applied force. Additionally, the upper forefoot leaf spring 60 can have a non-linear or variable force to deflection ratio such that the upper forefoot leaf spring 60 can deflect by a smaller amount with a smaller applied force, and a disproportionately larger amount with a larger applied force up to an upper deflection limit at which point the amount of deflection can decrease even when the applied force continues to increase. In this way, the upper forefoot leaf spring 60 can increase the overall stiffness of the prosthetic foot 10 as the amount of deflection in the upper forefoot leaf spring increases. Advantageously, this allows the prosthetic foot 10 to respond with a stiffer feel to the user when the user applies a greater force, such as when running, and a looser feel when the user applies a lesser force, such as when walking.

Figure 5:
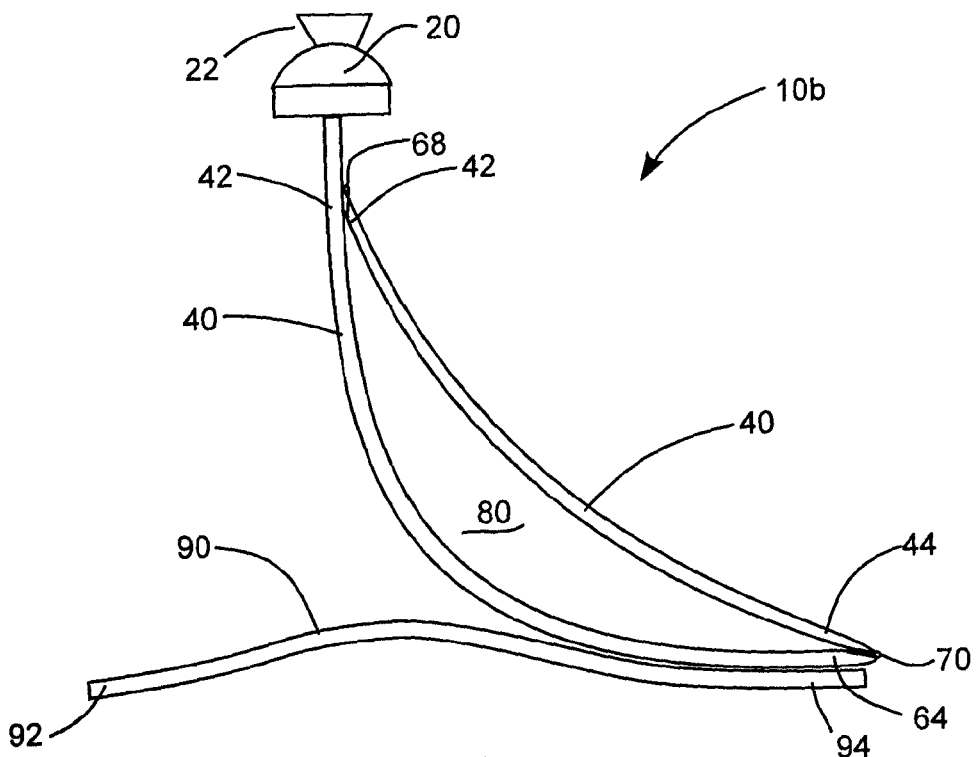
FIG. 5 is a side view of the prosthetic foot device of FIG. 1 shown with a foot plate.

Additionally, as shown in FIG. 5, the prosthetic foot 10b can also have a foot plate 90 that can extend underneath the lower forefoot leaf spring. The foot plate 90 can extend between a heel section 92 positioned at a heel location of a natural foot and a toe section 94 positioned at the toe location of a natural foot. The foot plate 90 can be formed of a composite fiber material with a resin and can be flexible to store energy and resilient to return energy.

Figure 6:
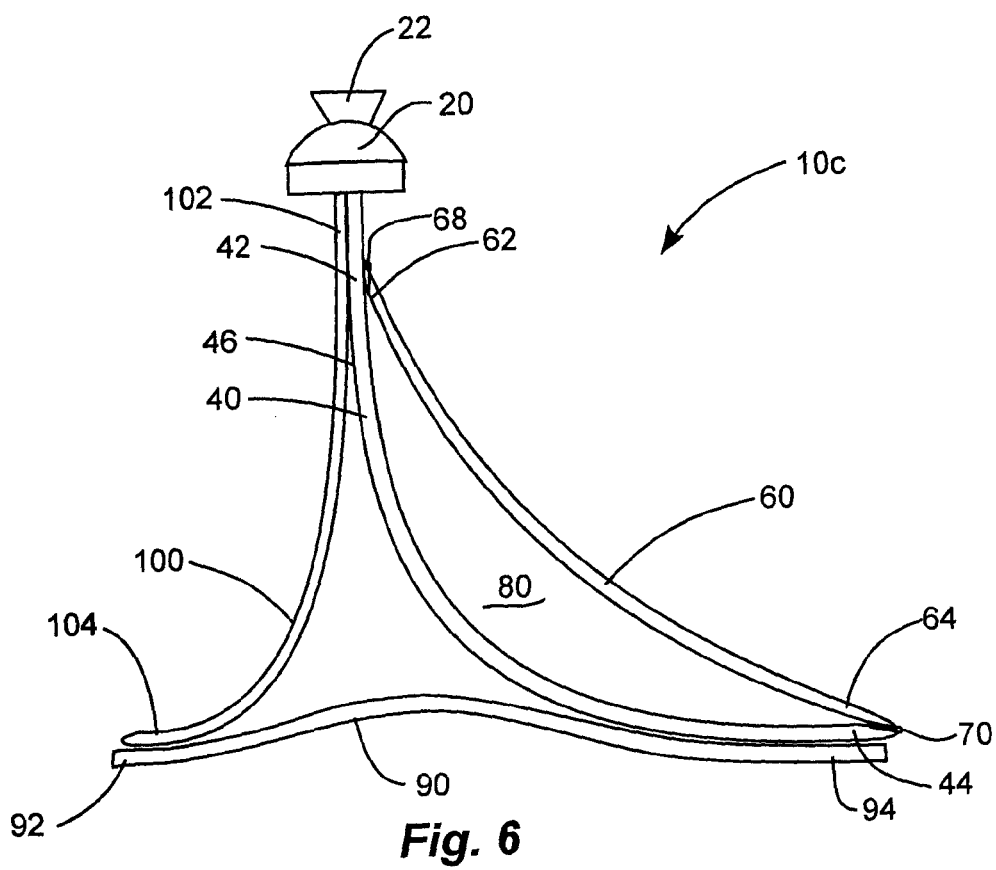
FIG. 6 is a side view of another prosthetic foot device in accordance with an embodiment of the present invention.

Referring to FIG. 6, the prosthetic foot 10c can also have a heel member 100. The heel member 100 can have an ankle section 102 adjacent the attachment section 20. In one embodiment, the heel member 100 can attach to a back or rearward side 46 of the lower forefoot leaf spring 40. In another embodiment, the heel member 100 and the lower forefoot leaf spring 40 can be coupled by the attachment section 20.

The heel member 100 can extend downward from the attachment section and rearward to a heel section 104. In one aspect, the heel section 104 of the heel member 100 can be disposed above the heel section 92 of the foot plate 90. In another aspect, the heel section 104 of the heel member 100 can be configured to contact the ground surface directly in the case where a foot plate is not used with the prosthetic foot 10.

Figure 7:
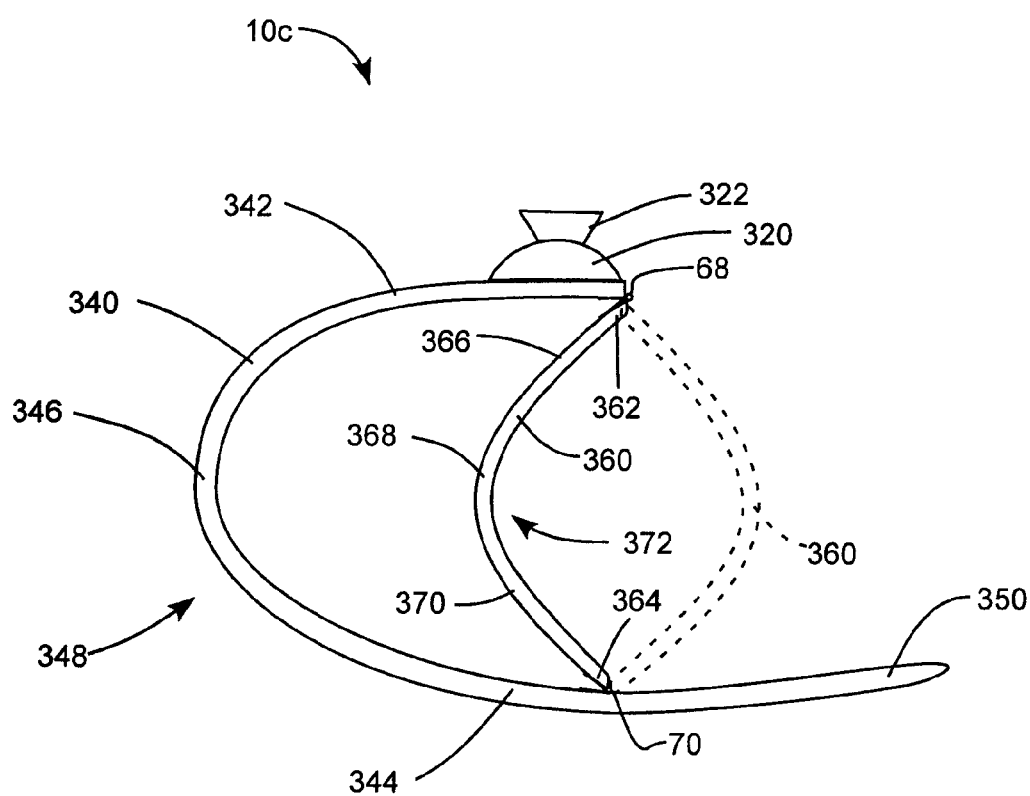
FIG. 7 is a side view of another prosthetic foot device in accordance with an embodiment of the present invention.

As illustrated in FIG. 7, a prosthetic foot device, indicated generally at 10d, is shown in accordance with another embodiment of the present invention for use by an amputee. The prosthetic foot device 10d can be similar in many respects to the prosthetic foot devices described above and shown in FIGS. 1-2 and 5-6. The prosthetic foot device 10d can have an attachment section, indicated generally at 320, an elongated primary lower forefoot leaf spring 340, and an elongated secondary upper forefoot leaf spring 360. The attachment of the lower and/or upper forefoot leaf springs to the attachment member can be essentially horizontal. At least one of the forefoot leaf spring, such as the lower forefoot leaf spring, can have an essentially horizontal attachment.

The attachment section 320 can include a connector or coupler 322 configured to attach to the stump of an amputee. The connector 322 can include a frustroconical connector, pyramidal connector, or the like.

The lower forefoot leaf spring 340 can extend between the attachment section 320 and a toe location of a natural foot. The lower forefoot leaf spring 340 can have an upper section 342, an ankle section 346, and a lower section 344 extending to the toe location 350. The lower forefoot leaf spring 340 can form a smooth and curving arc, indicated generally at 348. The upper section 342 can slope rearwardly and downwardly from the attachment section 320 to the ankle section 346. The lower section 344 can slope downwardly and forwardly from the ankle section 346 to the toe location 350. Thus, the lower forefoot leaf spring 340 can have a C-shaped curve.

The upper forefoot leaf spring 360 can extend approximately between the attachment section 320 and the lower section 344. The upper forefoot leaf spring 360 can be coupled at an upper end 362 to the upper section 342 of the lower forefoot leaf spring 340. Additionally, the upper forefoot leaf spring 360 can be coupled at a lower end 364 to the lower section 344 of the lower forefoot leaf spring 340.

The upper forefoot leaf spring 360 can have an upper section 366, an ankle section 368, and a lower section 370. The upper section 366 can slope rearwardly and downwardly from the upper end 362 to an ankle section 368. The lower section 370 can slope downwardly and forwardly from the ankle section 368 to the lower end 364. Thus, the upper forefoot leaf spring 360 can also form a smooth and curving arc with a C-shaped curve, indicated generally at 372. The upper forefoot leaf spring 360 can be arcuate and bend towards the lower forefoot leaf spring in a concave configuration (as shown in solid lines); or can be arcuate and bend away from the lower forefoot leaf spring in a convex configuration (as shown in dashed lines). However, the arc 372 of the upper forefoot leaf spring 360 can have more vertical orientation than the arc 348 of the lower forefoot leaf spring 340. Advantageously, this vertical orientation of the upper forefoot leaf spring 360 can provide added stiffness and resiliency to the prosthetic foot 10 making the foot more suited to high impact activities such as sprinting, running, cornering, hiking, and other athletic activities.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A prosthetic foot, comprising:
   an attachment member configured to be attached to a stump of an amputee at or above an ankle location;
   a pair of elongated forefoot leaf springs oriented one over another and that are flexible to store energy and resilient to return energy and with proximal ends coupled to one another at the attachment member and extending in an arc to distal ends coupled to one another at a toe location; and
   a pair of hinge connections each at a different one of the proximal and distal ends of the pair of elongated forefoot leaf springs and each coupling only the pair of forefoot leaf springs together.

2. A prosthetic foot in accordance with claim 1, further comprising:
   an open, uninterrupted gap between the forefoot leaf springs with intermediate portions of the pair of forefoot leaf springs are free to move with respect to one another during deflection.

3. A prosthetic foot in accordance with claim 1, wherein the pair of forefoot leaf springs together having a non-linear force deflection under loading during gait with an upper one of the pair of forefoot leaf springs increasing in stiffness when deflected by a lower one of the pair of forefoot leaf springs.

4. A prosthetic foot in accordance with claim 1, wherein the pair of forefoot leaf springs is oriented essentially vertical at the proximal ends.

5. A prosthetic foot in accordance with claim 1, wherein at least one of the pair of forefoot leaf springs is oriented essentially horizontal at the proximal end.

6. A prosthetic foot in accordance with claim 1, further comprising:
   a foot plate disposed under the pair of forefoot leaf springs and extending from a heel section at a heel location to the toe location.

7. A prosthetic foot in accordance with claim 6, further comprising:
   an elongated heel leaf spring with a proximal end affixed to the attachment member and extending in an arc to a distal end at the heel location.

8. A prosthetic foot in accordance with claim 1, wherein the proximal and distal ends of the pair of forefoot leaf springs are free to pivot with respect to one another during deflection of the pair of forefoot leaf springs.

9. A prosthetic foot in accordance with claim 1, wherein each of the pair of hinge connections have a pivot about which the proximal or distal ends pivot with respect to one another.

* * * * *